United States Patent [19]
Venham et al.

[11] Patent Number: 6,117,966
[45] Date of Patent: Sep. 12, 2000

[54] COATING COMPOSITIONS CONTAINING ALDIMINES AND POLYISOCYANATES

[75] Inventors: Lanny D. Venham, Paden City, W. Va.; Sharon D. Hicks, Pittsburgh; Douglas A. Wicks, Mt. Lebanon, both of Pa.

[73] Assignee: Bayer Corporation, Pittsburgh, Pa.

[21] Appl. No.: 08/171,550

[22] Filed: Dec. 21, 1993

[51] Int. Cl.[7] .................................................. C08G 18/32
[52] U.S. Cl. .............................. 528/68; 528/48; 528/49; 528/52; 528/59
[58] Field of Search ................................. 528/48, 49, 52, 528/59, 68

[56] References Cited

U.S. PATENT DOCUMENTS

| | | |
|---|---|---|
| 3,420,800 | 1/1969 | Haggis et al. . |
| 3,567,692 | 3/1971 | Haggis et al. . |
| 4,469,831 | 9/1984 | Bueltjer et al. ............................ 528/59 |
| 4,853,454 | 8/1989 | Merger et al. ............................. 528/59 |
| 5,214,086 | 5/1993 | Mormile et al. ......................... 524/237 |
| 5,243,012 | 9/1993 | Wicks et al. .............................. 528/58 |

OTHER PUBLICATIONS

"One Component Polyurethane Elastomers Based on Novel Polyaldimine", M. Aoki et al, Polyurethanes World Congress 1993–Oct. 10–13, 1993, pp. 341–345.

Huls—Vestamin A 139, Product Information Bulletin.

*Primary Examiner*—John M. Cooney, Jr.
*Attorney, Agent, or Firm*—Joseph C. Gil; Thomas W. Roy

[57] ABSTRACT

The present invention is directed to coating compositions which have long pot lives and may be rapidly cured under ambient conditions wherein the binder contains a) a polyisocyanate component containing i) 5 to 100% by weight of a monoallophanate and ii) 0 to 95% by weight of another polyisocyanate adduct, and b) an aldimine based on the reaction product of diamino dicyclohexyl methane with an aldehyde corresponding to the formula:

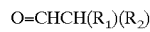

$$O=CHCH(R_1)(R_2)$$

wherein $R_1$ and $R_2$ may be the same or different and represent optionally substituted hydrocarbon radicals, or $R_1$ and $R_2$ together with the β-carbon atom form a cycloaliphatic or heterocyclic ring.

12 Claims, No Drawings

6,117,966

1

COATING COMPOSITIONS CONTAINING ALDIMINES AND POLYISOCYANATES

BACKGROUND OF THE INVENTION

1. Field of the Invention

The present invention is directed to coating compositions having long pot lives and short dry times under ambient conditions in which the binder is based on polyisocyanates containing allophanate groups and aldimines prepared from diamino dicyclohexyl methane.

2. Description of the Prior Art

Coating compositions which may be cured at room temperature are known. One-component coating compositions contain fully reacted polyurethanes as the binder. These compositions have the advantage that they are available as fully formulated systems which may be directly applied to suitable substrates without any preliminary steps except for mild stirring. Disadvantages of these systems are that large amounts of organic solvents are needed to reduce the viscosity of fully reacted, i.e., high molecular weight, polyurethanes. The coating compositions are cured by evaporation of the solvent which is objectionable from an environmental perspective. In addition, in order to solubilize the polyurethanes in organic solvents, they must be essentially linear polyurethanes. While such polyurethanes possess properties which are suitable for many applications, they do not provide certain properties, e.g., solvent resistance, which may be obtained from crosslinked polyurethanes.

Two-component coating compositions are also known. These compositions come in two containers. The first contains a polyisocyanate, while the second contains an isocyanate-reactive component, generally a polyol. The components are not mixed until they are ready to be used. One advantage of these compositions is that because the components are not pre-reacted to form a high molecular weight polymer, a suitable processing viscosity can be achieved without the need for large amounts of organic solvents. In addition, higher functional components can be used to obtain highly crosslinked coatings which possess properties which surpass those possessed by one-component coatings.

The disadvantages of these compositions is that they cannot be applied without a preliminary mixing step in which it is critical that the components are mixed in the right proportions. Special metering and mixing equipment is needed to conduct this process on a commercial scale. If the components are mixed in the wrong proportions, then the properties of the resulting coatings can be substantially affected. In addition, after the components are mixed they must be used in a timely fashion. If not, they continue to react until an unusable solid is finally obtained.

It is an object of the present invention to provide coating compositions which possess the advantages of the known one- and two-component coating compositions without possessing any of their disadvantages. This object may be achieved with the coating compositions according to the present invention wherein the binder is based on a polyisocyanate containing allophanate groups and an aldimine prepared from diamino dicyclohexyl methane. The advantages of these coating compositions are as follows:

1) They may be prepared as fully formulated systems in a manner similar to the one-component systems discussed above and do not require the special metering and mixing equipment required to formulate and mix two-component systems.
2) Because the components are not pre-reacted to form high molecular weight polymers, large amounts of solvents are not necessary to reduce the viscosity of the coating compositions.

2

3) Highly functional resins can be used to provide crosslinked coatings with exceptional properties.
4) The manufacturer can accurately formulate the compositions such that there is no need for on-site mixing and metering equipment.
5) Because of the excellent compatibility between the components, which is disclosed in copending application, Attorney's Docket No. Mo-4053, coatings prepared from the compositions possess excellent optical properties.
6) After the polyisocyanates and aldimines are mixed, they have long pot lives when compared at equivalent solids to coating compositions based on other aldimines, and yet rapidly cure under ambient conditions to form coatings when applied to substrates.

This last advantage of the compositions according to the invention is particularly surprising and unexpected because the known high solids coating compositions, which cure rapidly when applied to substrates, do not possess long pot lives. On the other hand, compositions which remain stable in storage (e.g., by blocking the polyisocyanate), do not cure rapidly when applied to substrates. Accordingly, it could not be expected that it would be possible to provide coating compositions which satisfy the requirements of storage stability and rapid cure under ambient conditions.

U.S. Pat. No. 3,420,800 and 3,567,692 disclose coating compositions containing polyisocyanates and either aldimines or ketimines. However, the coating compositions described in these references do not possess long pot lives, i.e., good storage stability, nor are the components compatible with each other resulting in unacceptable coatings. These references did not recognize the specific binder components described in accordance with the present invention, which necessary to obtain long pot lives and rapid cure.

SUMMARY OF THE INVENTION

The present invention is directed to coating compositions which have long pot lives and may be rapidly cured under ambient conditions wherein the binder contains a) polyisocyanate component containing
   i) 5 to 100% by weight of a monoallophanate and
   ii) 0 to 95% by weight of another polyisocyanate adduct, and
b) an aldimine based on the reaction product of diamino dicyclohexyl methane with an aldehyde corresponding to the formula:

O=CHCH($R_1$)($R_2$)

wherein $R_1$ and $R_2$ may be the same or different and represent optionally substituted hydrocarbon radicals, or $R_1$ and $R_2$ together with the β-carbon atom form a cycloaliphatic or heterocyclic ring.

DETAILED DESCRIPTION OF THE INVENTION

In accordance with the present invention the term "monoallophanate" means a polyisocyanate containing one allophanate group and formed from two isocyanate molecules and 1 monoalcohol molecule, and the term "polyallophanate" means a polyisocyanate containing more than one allophanate group. The term "(cyclo)-aliphatically bound isocyanate groups" means aliphatically and/or cycloaliphatically bound isocyanate groups.

Suitable polyisocyanates for use in the coating compositions of the present invention are polyisocyanates containing allophanate groups which are generated from monoalcohols. As disclosed in copending application, Attorney's Docket No. Mo-4053, these polyisocyanates have excellent compatibility with aldimines. Because of this compatibility, the resulting coatings have improved clarity, gloss and DOI when compared to coatings prepared from compositions which do not possess these allophanate groups. In addition to using the polyisocyanates containing allophanate groups as the only polyisocyanate component, these polyisocyanates may also be blended with other monomeric polyisocyanates, polyisocyanate adducts or NCO prepolymers to improve their compatibility with aldimines.

The polyisocyanates containing allophanate groups may be prepared by reacting monourethanes with monomeric diisocyanates at elevated temperatures to form allophanate groups. The monourethanes may be prepared in an initial step by reacting monomeric diisocyanates with monoalcohols or they may be prepared in situ by adding the monoalcohols to an excess of monomeric diisocyanates. Suitable processes for preparing these products are described in U.S. Pat. Nos. 4,160,080 and 3,769,318, the disclosures of which are herein incorporated by reference.

Examples of suitable diisocyanates to be used as starting materials for preparing the polyisocyanates containing allophanate groups include organic diisocyanates represented by the formula

R(NCO)$_2$ wherein R represents an organic group obtained by removing the isocyanate groups from an organic diisocyanate having aromatically or (cyclo)aliphatically bound isocyanate groups and a molecular weight of 112 to 1,000, preferably 140 to 400. Preferred diisocyanates for the process according to the invention are those represented by the above formula wherein R represents a divalent aliphatic hydrocarbon group having 4 to 18 carbon atoms, a divalent cycloaliphatic hydrocarbon group having 5 to 15 carbon atoms, a divalent araliphatic hydrocarbon group having 7 to 15 carbon atoms or a divalent aromatic hydrocarbon group having 6 to 15 carbon atoms.

Examples of the organic diisocyanates which are particularly suitable for the process include 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3- and -1,4-diisocyanate, 1-isocyanato-2-isocyanatomethyl cyclopentane, 1-isocyanato-3-isocyanatomethyl-3,5,5-trimethyl-cyclohexane (isophorone diisocyanate or IPDI), bis-(4-isocyanatocyclohexyl)-methane, 2,4'-dicyclohexylmethane diisocyanate, 1,3- and 1,4-bis (isocyanatomethyl)-cyclohexane, bis-(4-isocyanato-3-methyl-cyclohexyl)-methane, α,α,α',α'-tetramethyl-1,3- and/or -1,4-xylylene diisocyanate, 1-isocyanato-1-methyl-4 (3)-isocyanatomethyl cyclohexane, 2,4- and/or 2,6-hexahydrotoluylene diisocyanate, 1,3- and/or 1,4-phenylene diisocyanate, 2,4- and/or 2,6-toluylene diisocyanate, 2,4- and/or 4,4'-diphenylmethane diisocyanate, 1,5-diisocyanato naphthalene and mixtures thereof. Aromatic polyisocyanates containing 3 or more isocyanate groups such as 4,4', 4"-triphenylmethane diisocyanate and polyphenyl polymethylene polyisocyanates obtained by phosgenating aniline/formaldehyde condensates may also be used. Preferred diisocyanates are 1,6-hexamethylene diisocyanate, isophorone diisocyanate and bis-(4-isocyanatocyclohexyl)-methane. 1,6-hexamethylene diisocyanate (HDI) is especially preferred.

It is also possible in accordance with the present invention to use blends of the previously mentioned diisocyanates with monoisocyanates or polyisocyanates having 3 or more isocyanate groups, provided that the isocyanate groups are (cyclo)aliphatically bound.

Suitable monoalcohols which may be used to prepare the polyisocyanates containing allophanate groups include aliphatic, cycloaliphatic, araliphatic or aromatic monoalcohols. The monoalcohols may be linear, branched or cyclic, contain at least one carbon atom and have a molecular weight of up to 2500. The monoalcohols may optionally contain other hetero atoms in the form of, e.g., ether groups, ester groups, etc. However, the monoalcohols preferably do not contain hetero atoms other than the hydroxyl group itself. The molar ratio of monoalcohol to diisocyanate is about 0.01 to 0.5, preferably about 0.04 to 0.2. Preferred monoalcohols are hydrocarbon monoalcohols and monoalcohols containing ether groups.

The hydrocarbon monoalcohols preferably contain 1 to 36, more preferably 1 to 20 and most preferably 1 to 8 carbon atoms. Examples of suitable monoalcohols include methanol, ethanol, n-propanol, isopropanol, n-butanol, isobutanol and tert. butanol, n-pentanol, 2-hydroxy pentane, 3-hydroxy pentane, the isomeric methyl butyl alcohols, the isomeric dimethyl propyl alcohols, neopentyl alcohol, n-hexanol, n-heptanol, n-octanol, n-nonanol, 2-ethyl hexanol, trimethyl hexanol, cyclohexanol benzyl alcohol, phenol, the cresols, the xylenols, the trimethylphenols, decanol, dodecanol, tetradecanol, hexadecanol, octadecanol, 2,6,8-trimethyinonanol, 2-t-butyl-cyclohexanol, 4-cyclohexyl-1-butanol, 2,4,6,-trimethyl benzyl alcohol, branched chain primary alcohols and mixtures thereof (which are available from Henkel under the Standamul trademark) and mixtures of linear primary alcohols (which are available from Shell under the Neodol trademark).

Preferred ether-containing monoalcohols include ethoxy methanol, methoxy ethanol, ethoxy ethanol, the isomeric methoxy or ethoxy propanols, the isomeric propoxy methanols and ethanols, the isomeric methoxy butanols, the isomeric butoxy methanols, furfuralcohol and other monoalcohols which have a molecular weight of up to 2500 and are based on ethylene oxide, propylene oxide and/or butylene oxide.

It is also possible in accordance with the present invention to use mixtures of the previously described monoalcohols.

The polyisocyanates containing allophanate groups may be blended with the previously described monomeric diisocyanates, with other polyisocyanate adducts or with NCO prepolymers to improve their compatibility with aldimines. These other polyisocyanate adducts include those containing isocyanurate, uretdione, biuret, urethane, allophanate, carbodiimide and/or oxadiazinetrione groups. The polyisocyanates adducts have an average functionality of 2 to 6 and an NCO content of 5 to 30% by weight.

1) Isocyanurate group-containing polyisocyanates which may be prepared as set forth in DE-PS 2,616,416, EP-OS 3,765, EP-OS 10,589, EP-OS 47,452, U.S. Pat. Nos. 4,288, 586 and 4,324,879. The isocyanato-isocyanurates generally have an average NCO functionality of 2.5 to 4.5, preferably 3 to 3.5 and an NCO content of 5 to 30%, preferably 10 to 25% and most preferably 15 to 25% by weight.

2) Uretdione diisocyanates which may be prepared by oligomerizing a portion of the isocyanate groups of a diisocyanate in the presence of a trialkyl phosphine catalyst and which may be used in admixture with other aliphatic and/or cycloaliphatic polyisocyanates, particularly the isocyanurate group-containing polyisocyanates set forth under (1) above.

3) Biuret group-containing polyisocyanates which may be prepared according to the processes disclosed in U.S. Pat. Nos. 3,124,605; 3,358,010; 3,644,490; 3,862,973; 3,906,126; 3,903,127; 4,051,165; 4,147,714; or 4,220,749 by using co-reactants such as water, tertiary alcohols, primary and secondary monoamines, and primary and/or secondary diamines. These polyisocyanates preferably have an NCO content of 18 to 22% by weight and an average NCO functionality of 2.5 to 4.5, preferably 3 to 3.5.

4) Urethane group-containing polyisocyanates which may be prepared in accordance with the process disclosed in U.S. Pat. No. 3,183,112 by reacting excess quantities of polyisocyanates, preferably diisocyanates, with low molecular weight glycols and polyols having molecular weights of less than 400, such as trimethylol propane, glycerine, 1,2-dihydroxy propane and mixtures thereof. The urethane group-containing polyisocyanates have a most preferred NCO content of 12 to 20% by weight and an (average) NCO functionality of 2.5 to 4.5, preferably 2.5 to 3.

5) Allophanate group-containing polyisocyanates which may be prepared as described above from difunctional or higher functional, low or high molecular weight polyols as described in U.S. Pat. Nos. 3,769,318, 4,160,080 and 4,177,342. The allophanate group-containing polyisocyanates have a most preferred NCO content of 12 to 21% by weight and an (average) NCO functionality of 2.5 to 4.5.

6) Carbodiimide group-containing polyisocyanates which may be prepared by oligomerizing di- or polyisocyanates in the presence of known carbodiimidization catalysts as described in DE-PS 1,092,007, U.S. Pat. No. 3,152,162 and DE-OS 2,504,400, 2,537,685 and 2,552,350.

7) Polyisocyanates containing oxadiazinetrione groups and containing the reaction product of two moles of a diisocyanate and one mole of carbon dioxide.

Preferred polyisocyanate adducts are the polyisocyanates containing isocyanurate groups, biuret groups or urethane groups.

Instead of using mixtures of polyisocyanates containing allophanate groups and polyisocyanate adducts which have been separately prepared, in certain cases it is possible to prepare these mixtures in one step. For example, mixtures of polyisocyanates containing allophanate groups and isocyanurate groups may be prepared by trimerizing the isocyanate starting material in the presence of trimerization catalysts and monoalcohols. Suitable catalysts and methods of the production of these polyisocyanate mixtures are disclosed, e.g., in U.S. Pat. Nos. 5,124,427, 5,208,334 and 5,235,018, the disclosures of which are herein incorporated by reference, and in copending applications U.S. Ser. Nos. 08/003,779, and 08/081,923, the disclosures of which are herein incorporated by reference.

In addition to mixtures of polyisocyanates containing allophanate groups and isocyanurate groups, it is also possible to directly prepare mixtures of polyisocyanates containing allophanate groups and biuret groups by biuretizing the isocyanate starting material in the presence of a biuretizing agent and a monoalcohol. It is less preferred to directly prepare polyisocyanates containing allophanate groups and urethane groups because in addition to forming allophanate groups from monourethanes, allophanate groups will also be formed from the polyisocyanates adducts containing more than one urethane group. This results in a substantial increase in the viscosity of the resulting product.

Preferred mixtures of polyisocyanates are those containing allophanate and isocyanurate groups or allophanate and biuret groups, more preferably allophanate and isocyanurate groups. The ratio of monoisocyanurate groups to monoallophanate groups present in these more preferred polyisocyanates is about 10:1 to 1:10, preferably about 5:1 to 1:7. These values may be determined by gel permeation chromatography (GPC) by determining the areas under the peaks for the monoisocyanurate and monoallophanate groups. The polyisocyanates according to the invention generally contain a total of less than 2, preferably less than 1% of free (unreacted) monomeric diisocyanates.

In addition to monomeric polyisocyanates and polyisocyanates adducts, the polyisocyanates containing allophanate groups may also be blended with NCO prepolymers to improve their compatibility with aldimines.

The NCO prepolymers, which may also be used as the polyisocyanate component in accordance with the present invention, are prepared from the previously described monomeric polyisocyanates or polyisocyanate adducts, preferably monomeric diisocyanates, and organic compounds containing at least two isocyanate-reactive groups, preferably at least two hydroxy groups. These organic compounds include high molecular weight compounds having molecular weights of 400 to about 6,000, preferably 800 to about 3,000, and optionally low molecular weight compounds with molecular weights below 400. The molecular weights are number average molecular weights ($M_n$) and are determined by end group analysis (NH number). Products obtained by reacting polyisocyanates exclusively with low molecular weight compounds are polyisocyanates adducts containing urethane groups and are not considered to be NCO prepolymers.

Examples of the high molecular weight compounds are polyester polyols, polyether polyols, polyhydroxy polycarbonates, polyhydroxy polyacetals, polyhydroxy polyacrylates, polyhydroxy polyester amides and polyhydroxy polythioethers. The polyester polyols, polyether polyols and polyhydroxy polycarbonates are preferred. Further details concerning the low molecular weight compounds and the starting materials and methods for preparing the high molecular weight polyhydroxy compounds are disclosed in U.S. Pat. No. 4,701,480, herein incorporated by reference.

These NCO prepolymers generally have an isocyanate content of about 0.5 to 30% by weight, preferably about 1 to 20% by weight, and are prepared in known manner by the reaction of the above mentioned starting materials at an NCO/OH equivalent ratio of about 1.05:1 to 10:1 preferably about 1.1:1 to 3:1. This reaction may take place in a suitable solvent which may optionally be removed by distillation after the reaction along with any unreacted volatile starting polyisocyanates still present. In accordance with the present invention NCO prepolymers also include NCO semi-prepolymers which contain unreacted starting polyisocyanates in addition to the urethane group-containing prepolymers.

In mixtures with monomeric polyisocyanates, polyisocyanate adducts or NCO prepolymers to provide improved compatibility, the polyisocyanates containing allophanate groups should be present in an amount of at least 5% by weight, preferably at least 25% by weight and more preferably at least 40% by weight, based on the solids content of the polyisocyanate component.

It is also possible in accordance with the present invention to use polyisocyanates containing allophanate groups and, e.g., isocyanurate groups, to compatibilize other polyisocyanate adducts or NCO prepolymers, provided that the resulting mixture contains the previously disclosed amounts of polyisocyanates containing allophanate groups.

Suitable aldimines for use in the coating compositions according to the present invention are those prepared from the isomers of diamino dicylohexyl methane, i.e., the 4,4'-, 2,4'- and 2,2'-isomers. The preferred isomer is bis-(4-aminocyclohexyl)-methane, which may be used in admixture with the other isomers.

Suitable aldehydes are those corresponding to the formula $$O=CHCH(R_1)(R_2)$$

wherein $R_1$ and $R_2$ may be the same or different and represent optionally substituted hydrocarbon radicals, preferably containing 1 to 10, more preferably 1 to 6, carbon atoms, or $R_1$ and $R_2$ together with the β-carbon atom form a cycloaliphatic or heterocyclic ring.

Examples of suitable aldehydes include isobutyraldehyde, 2-ethyl hexanal, 2-methyl butyraldehyde, 2-ethyl butyraldehyde, 2-methyl valeraidehyde, 2,3-dimethyl valeraldehyde, 2-methyl undecanal and cyclohexane carboxaldehyde. Isobutyraldehyde is especially preferred.

The aldimines may be prepared in known manner by reacting the polyamines with the aldehydes either in stoichiometric amounts or with an excess of aldehyde. The excess aldehyde and the water which is produced can be removed by distillation. The reactions may also be carried out in solvents, other than ketones. The solvents may also be removed by distillation after completion of the reaction.

The quantities of components a) and b) are chosen to provide an equivalent ratio of isocyanate groups to aldimine groups of 0.5:1 to 20:1, preferably 0.8:1 to 3:1 and more preferably 1:1 to 2:1.

In addition to the binder components, the coating compositions may also contain the known additives from coatings technology, such as fillers, pigments, softeners, high-boiling liquids, catalysts, UV stabilizers, anti-oxidants, microbiocides, algicides, dehydrators, thixotropic agents, wetting agents, flow enhancers, matting agents, anti-slip agents, aerators and extenders. The additives are chosen based on the requirements of the particular application and their compatibility with components a) and b). The coating compositions may be applied to the substrate to be coated by conventional methods such as brushing, painting, rolling, pouring or spraying.

The coating compositions according to the invention have long pot lives and provide coatings which have relatively fast dry times. The coatings are also characterized by high hardness, elasticity, very good resistance to chemicals, high gloss, good weather resistance, good environmental etch resistance and good pigmenting qualities.

It is believed that the combination of fast dry times and good storage stability is due to the fact that water catalyzes the reaction between the polyisocyanate and the aldimine. The prior art indicates that the curing mechanism takes place by hydrolyzing the aldimine to the amine which then reacts with the isocyanate. This is not the mechanism which takes place in accordance with the present invention. This is easily confirmed by the fact that aldehydes are not released during the curing reaction. The direct reaction between the aldimines and polyisocyanates does not take place in the absence of catalysts such as atmospheric moisture, which accounts for the excellent storage stability. However, after the coating composition has been applied to a suitable substrate, the same components which did not react when present in admixture in storage, rapidly react to form a coating. The reason for this phenomenon is believed to be the catalytic effect of atmospheric moisture.

The coatings prepared from the coating compositions according to the invention are also characterized by a combination of hardness and flexibility which cannot be obtained from aldimines prepared from diamines other than dicylohexyl methane diamines. And only aldimines prepared from the diamino dicyclohexyl methane can also provide the combination of long pot lives and fast dry times.

The invention is further illustrated, but is not intended to be limited, by the following examples in which all parts and percentages are by weight unless otherwise specified.

EXAMPLES

The following starting materials were used in the examples:

Polyisocyanate 1

To a 500 ml 3-neck flask equipped with a gas bubbler, mechanical stirrer, thermometer and condenser were added 301.7 grams of hexamethylene diisocyanate and 13.3 grams of 1-butanol. Dry nitrogen was bubbled through the stirred reaction mixture while it was heated at 60° C. When the urethane reaction was complete (about 1 hour), the temperature was raised to 90° C. To the reaction mixture at 90° C. were added 0.214 parts of a 4.4% solution of trimethylbenzylammonium hydroxide dissolved in 1-butanol. The reaction temperature was maintained at 90 to 100° C. When the reaction mixture reached NCO contents of 40.1% and 37.0%, an additional 0.12 parts of the catalyst solution was added. When the reaction mixture reached an NCO content of 34.8%, the reaction was stopped by adding 0.214 parts of di-(2-ethylhexyl) phosphate. The excess monomer was removed by thin film evaporation to provide an almost colorless, clear liquid having a viscosity of 630 mPa.s (25° C.), an NCO content of 19.7%, and a free monomer (HDI) content of 0.35%. The yield was 48.6%. The yield was calculated by determining the percentage of free hexamethylene diisocyanate in the product prior to distillation.

Aldimine 1

The aldimine of bis-(4-aminocyclohexyl)-methane and isobutraldehyde was prepared by initially charging 1514.3 parts (21 equivalents) of isobutyraldehyde and then slowly charging 2104.0 parts (20 equivalents) of bis-(4-aminocyclohexyl)-methane over a period of thirty minutes to avoid an exotherm. After the addition of the diamine the reaction mixture was stirred for one hour. At this time stirring was stopped and water was allowed to settle to the bottom of the reactor. As much water as possible was drained from the bottom of the reactor. The reaction mixture was then heated to 100° C. to remove excess isobutyraldehyde. While maintaining a temperature of 100° C., a vacuum of approximately 20 mm Hg was applied to remove any final traces of aldehyde. Thereafter the vacuum was increased to 1 mm Hg to remove water until the water content was less than 0.05% (approximately 1 to 3 hours.) The aldimine had a viscosity of 100 mPa.s at 25° C., an equivalent weight of 159.3, an APHA color of 70, a purity as determined by GPC of 93.5% and a water content of less than 0.05%.

Aldimine 2

The aldimine of isophorone diamine and isobutyraldehyde, available from Hüls as Vestamin A-139.

Aldimine 3

The aldimine of bis-(4-aminocyclohexyl)-methane and 2-ethyl hexanal was prepared using the procedure described for aldimine 1.

Ketimine 1

The ketimine of bis-(4-aminocyclohexyl)-methane and methyl isobutyl ketone.

Ketimine 2

The ketimine of isophorone diamine and methyl isobutyl ketone, available from Miles as Desmophen LS 2965.

Polyol 1

A polyester polyol having an OH equivalent weight of 740, an OH content of 2.3% and a functionality of about 5, present as a 70% solution in butyl acetate and prepared from 20.3 parts of a fatty acid mixture (Prifac 7990, available from Unichema International), 14.9 parts benzoic acid, 1.6 parts maleic anhydride and 27.5 parts phthalic anhydride.

Additive 1

An acrylate copolymer (available as Byk 358 from Byk Chemie).

Example 1

To prepare the coating compositions, 1.0 equivalent of the imine and 1.1 equivalents of the polyisocyanate set forth in Table 3, and sufficient n-butyl acetate to obtain a coating composition having a volatile organic content (VOC) of 2.0 lbs/gal were added sequentially to a 6 oz. container and stirred for one minute. After stirring a 3 mil drawdown on glass was immediately prepared and the resulting film was placed in a 23° C./50% relative humidity chamber with a 6 hour and a 1 hour Gardner Drytime recorder on the film. The Gardner dry time was determined using a Gardner Circular Drying Time Recorder. Set-to-touch—During the first stage of drying the film is mobile and partially flows back into the scribed channel. The film may be considered "set-to-touch" when it no longer flows back and the stylus begins to leave a clear channel.

Surface-dry—when sytlus no longer leaves clear channel, but begins to rupture the dry upper layer of the curing film, the film is considered to be "surface-dry."

Hard-dry—when the stylus no longer ruptures the film, but moves freely upon the surface, the cross-section of the film may be considered to have reached the "hard-dry" condition.

Mar-free—When the stylus no longer mars the surface of the film at all the film may be considered to be "mar-free."

Cotton ball dry is the time after which it is possible to apply and remove a cotton ball without it sticking to the surface of the coating.

The remainder of the coating composition was monitored for viscosity buildup using a #2 Zahn cup. The results for the dry times and viscosity buildup are set forth in Tables 1 and 2.

TABLE 1

Comparison of Pot Lives of Coating Compositions Containing Polyisocyanate 1

| Viscosity (seconds) | Ketimine 1 (Comp) | Ketimine 2 (Comp) | Aldimine 1 | Aldimine 2 (Comp) |
|---|---|---|---|---|
| initial | 16.6 | 18.7 | 15.5 | 15.0 |
| 30 minutes | 17.1 | 21.6 | 15.8 | 15.2 |
| 60 minutes | 17.8 | 24.3 | 16.4 | 15.5 |
| 120 minutes | 19.4 | 31.3 | 17.1 | 15.7 |

TABLE 2

Comparison of Dry Times of Coating Compositions Containing Polyisocyanate 1

| Gardner Dry Time (hours) | Ketimine 1 | Ketimine 2 | Aldimine 1 | Aldimine 2 |
|---|---|---|---|---|
| Set to touch | 1 | 1 | 0.25 | 1.5 |
| Surface Dry | 2 | 2 | 0.5 | 2.5 |
| Hard Dry | 3 | 4 | 1 | 4 |
| Mar Free | 5 | 5 | 2 | 5 |

TABLE 2-continued

Comparison of Dry Times of Coating Compositions Containing Polyisocyanate 1

| Gardner Dry Time (hours) | Ketimine 1 | Ketimine 2 | Aldimine 1 | Aldimine 2 |
|---|---|---|---|---|
| Cotton ball Dry (hours) | 2.0–2.5 | 2.5 | 0.5 | 2.0–2.5 |

Tables 1 and 2 demonstrate that coating compositions formulated with aldimine 1 (according to the invention) exhibited shorter dry times while maintaining longer pot lives than those formulated with ketimines 1 and 2 or aldimine 2.

Example 2

To prepare the coating composition a 50/50 blend of aldimine 1 and polyol 1, 1.1 equivalent of polyisocyanate 2, 0.1% (based on resins solids) of additive 1 and sufficient n-butyl acetate to obtain a coating composition with a volatile organic content (VOC) of 3.59 lbs/gal were added sequentially to a 6 oz. container and stirred for one minute. The coating composition had a solids content of 56.73%. Coatings were prepared as described in Example 1 and the viscosity of the remainder of the coating composition was monitored for viscosity buildup using a Brookfield Viscometer. The results for the dry times and viscosity buildup are set forth in Table 3.

TABLE 3

| Viscosity, Brookfield #2 spindle, 60 rpm (centipoise) | |
|---|---|
| initial | 50 |
| 15 minutes | 85 |
| 30 minutes | *175 |
| Gardner Dry Time (minutes) | |
| Set to touch | 1 |
| Surface Dry | 4 |
| Hard Dry | 13 |
| Mar Free | 75 |

*above sprayable viscosity

Table 6 demonstrates that introduction of a polyol into the formulation significantly reduces the sprayable pot life of the system even in the presence of the aldimine.

Example 3

A coating was prepared from polyisocyanate 1 and aldimine 3 using the procedure of Example 1. The resulting coating was clear and free of defects.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A coating composition which has a long pot life and may be rapidly cured under ambient conditions wherein the binder contains a) a polyisocyanate component containing
   i) 5 to 100% by weight of a monoallophanate and
   ii) 0 to 95% by weight of another polyisocyanate adduct, and b) an aldimine based on the reaction product of diamino dicyclohexyl methane with an aldehyde corresponding to the formula:

wherein $R_1$ and $R_2$ may be the same or different and represent optionally substituted hydrocarbon radicals, or $R_1$ and $R_2$ together with the β-carbon atom form a cycloaliphatic or heterocyclic ring, wherein components a) and b) are present in amounts which are sufficient to provide an equivalent ratio of isocyanate groups to aldimine groups of 0.5:1 to 20:1.

2. The coating composition of claim 1 wherein component ai) is present in an amount of at least 25% by weight.

3. The coating composition of claim 1 wherein component a) is a polyisocyanate blend containing monoisocyanurate groups and monoallophanate groups in a ratio of 10:1 to 1:10.

4. The coating composition of claim 3 wherein said polyisocyanate blend is prepared from 1,6-hexamethylene diisocyanate.

5. A coating composition which has a long pot life and may be rapidly cured under ambient conditions wherein the binder contains
a) a polyisocyanate component containing
   i) 5 to 100% by weight of a monoallophanate and
   ii) 0 to 95% by weight of another polyisocyanate adduct, and
b) an aldimine based on the reaction product of diamino dicyclohexyl methane with an aldehyde corresponding to the formula:

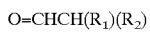

wherein $R_1$ and $R_2$ may be the same or different and represent hydrocarbon radicals containing 1 to 6 carbon atoms, wherein components a) and b) are present in amounts which are sufficient to provide an equivalent ratio of isocyanate groups to aldimine groups of 0.5:1 to 20:1.

6. The coating composition of claim 5 wherein said aldehyde comprises isobutyraldehyde.

7. The coating composition of claim 5 wherein component ai) is present in an amount of at least 25% by weight.

8. The coating composition of claim 6 wherein component ai) is present in an amount of at least 25% by weight.

9. The coating composition of claim 5 wherein component a) is a polyisocyanate blend containing monoisocyanurate groups and monoallophanate groups in a ratio of 10:1 to 1:10.

10. The coating composition of claim 6 wherein component a) is a polyisocyanate blend containing monoisocyanurate groups and monoallophanate groups in a ratio of 10:1 to 1:10.

11. The coating composition of claim 9 wherein said polyisocyanate blend is prepared from 1,6-hexamethylene diisocyanate.

12. The coating composition of claim 10 wherein said polyisocyanate blend is prepared from 1,6-hexamethylene diisocyanate.

* * * * *